United States Patent [19]
Ushida

[11] Patent Number: 4,485,369
[45] Date of Patent: Nov. 27, 1984

[54] SENSOR FOR MEASURING AIR-FUEL RATIO

[75] Inventor: Yoshiro Ushida, Toyoake, Japan

[73] Assignee: NGK Spark Plug Co., Ltd., Nagoya, Japan

[21] Appl. No.: 331,753

[22] Filed: Dec. 17, 1981

[30] Foreign Application Priority Data

Feb. 10, 1981 [JP] Japan .................................. 56-18301

[51] Int. Cl.³ .......................................... G01N 27/12
[52] U.S. Cl. .................................................... 338/34
[58] Field of Search .................. 204/425, 408; 338/34; 422/94, 95, 96, 97, 98

[56] References Cited

U.S. PATENT DOCUMENTS

| 4,147,513 | 4/1979 | Bienkowski et al. | 338/34 X |
| 4,224,113 | 9/1980 | Kimura et al. | 204/1 T |
| 4,233,033 | 11/1980 | Eifler et al. | 338/34 X |
| 4,303,613 | 12/1981 | Yasuda et al. | 422/95 |
| 4,322,383 | 3/1982 | Yasuda et al. | 422/95 |
| 4,322,968 | 4/1982 | Takami et al. | 338/34 X |
| 4,327,054 | 4/1982 | Yasuda et al. | 422/95 |

FOREIGN PATENT DOCUMENTS 130645 10/1981 Japan .................................... 422/98

Primary Examiner—G. L. Kaplan
Attorney, Agent, or Firm—Fleit, Jacobson, Cohn & Price

[57] ABSTRACT

A sensor for measuring air-fuel ratio, comprising a porous oxygen ion-conductive solid electrolyte sintered body having a pellet-like shape, and two heat-resistant metal wires embedded therein at a given interval, can measure accurately and easily the air-fuel ratio of a gas in a lean side, wherein the air-fuel ratio is not less than the theoretical air-fuel ratio.

The solid electrolyte may be either zirconia or thoria containing as a stabilizer yttria, calcia or magnesia and having an apparent porosity of from about 5% to about 40%.

2 Claims, 7 Drawing Figures ature of the present invention is to provide

SENSOR FOR MEASURING AIR-FUEL RATIO

BACKGROUND OF THE INVENTION (1) Field of the Invention

The present invention relates to a sensor for measuring the air-fuel ratio of gases to be measured, such as exhaust gas and the like (hereinafter, gas to be measured may be merely referred to as gas) from the oxygen concentration in these gases by measuring the electrical resistance of the sensor, and a method of measuring the air-fuel ratio by using said sensor.

(2) Description of the Prior Art

There has been proposed to drive a motorcar at a lean side, wherein the air-fuel ratio of an intake mixture is higher than the theoretical air-fuel ratio (excess air ratio $\lambda=1$) in order to lower the fuel consumption of motorcar engine and to purify the exhaust gas, and such a sensor is demanded that can measure accurately the air-fuel ratio within the range of the excess air ratio $\lambda$ of not less than 1. Japanese Patent Laid Open Application No. 62,349/80 discloses a method, wherein a direct current having a value lower than the critical electric current value, at which the electromotive force does not vary against the air-fuel ratio other than the theoretical air-fuel ratio, is flowed between the two electrodes in an oxygen concentration cell comprising a measuring-side electrode layer, an oxygen ion-conductive solid electrolyte layer, a reference-side electrode layer and a membrane layer superposed one upon another, whereby the air-fuel ratio is measured by the electromotive force caused between the above described electrodes. However, in this method for measuring air-fuel ratio, the relation between the excess air ratio $\lambda$ and the above described electromotive force is not linear in the region of almost $\lambda=1$ within the range of the excess air ratio $\lambda$ of not less than 1. Therefore, this method is disadvantageous in the measuring of air-fuel ratio. Moreover, the sensor disclosed in the Japanese patent application has a drawback that, when it is intended to arrange the sensor in a plug and to use the plug as a plug for measuring air-fuel ratio, the structure of the plug is complicated.

SUMMARY OF THE INVENTION

It is an object of the present invention to provide a novel sensor for measuring air-fuel ratio, which is adapted to be used as a plug for measuring air-fuel ratio, and which can be set so that the electrical property between the electrodes is linearly varied depending upon the variation of the excess air ratio $\lambda$ of a gas within a wide range of the excess air ratio $\lambda$ of not less than 1, whereby the air-fuel ratio of the gas can be accurately and easily measured in the lean side, wherein the amount of fuel is smaller than the theoretical air-fuel ratio.

Another object of the present invention is to provide a method of measuring the air-fuel ratio of a gas by using the above described sensor.

That is, the feature of the present invention is to provide a sensor for measuring air-fuel ratio of a gas wherein the oxygen content in the gas is sensed through the measurement of the electrical resistance of the sensor, comprising a porous oxygen ion-conductive solid electrolyte sintered body having a pellet-like shape, and two heat-resistant metal wires embedded therein at a given interval for measuring the electrical resistance.

Another feature of the present invention is to provide a method of measuring the air-fuel ratio of a gas, comprising arranging in the gas a sensor for measuring air-fuel ratio, which comprises a porous oxygen ion-conductive solid electrolyte sintered body having a pellet-like shape, and two heat-resistant metal wires embedded therein at a certain interval; flowing a direct current having a certain value between the above described metal wires, setting the sensor so that the electrical voltage drops between the metal wires is linearly varied depending upon the variation of the excess air ratio $\lambda$ of the gas in a wide range within the excess air ratio $\lambda$ of not less than 1, and measuring the air-fuel ratio of the gas from the variation of the electrical voltage drop between the metal wires.

DESCRIPTION OF THE PREFERRED EMBODIMENT

Figure 1:
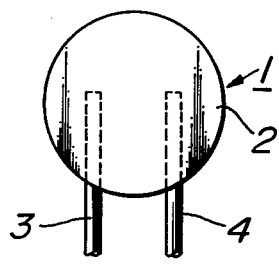
FIG. 1 is a plan view of a sensor for measuring air-fuel ratio according to the present invention.

The present invention will be explained referring to the drawings.

Figure 2:
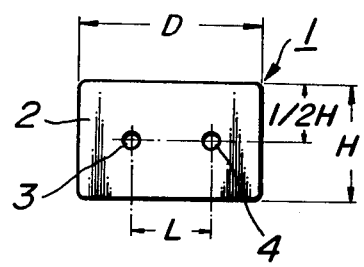
FIG. 2 is a front view of the sensor illustrated in FIG. 1.

FIGS. 1 and 2 illustrate one embodiment of a sensor for measuring air-fuel ratio according to the present invention. The sensor 1 for measuring air-fuel ratio comprises a porous disc-shaped oxygen ion-conductive solid electrolyte sintered body 2 having a diameter D of 3.0 mm and a thickness H of 1.9 mm; and a pair of metal wires 3 and 4 made of platinum and having a diameter of 0.4 mm, said metal wires being embedded at one end in parallel to each other in the sintered body 2 at an interval of 2 mm. The solid electrolyte sintered body 2 of this embodiment is formed of $ZrO_2$ stabilized with $Y_2O_3$ and has an apparent porosity of 22%. However, in the present invention, other oxygen ion-conductive solid electrolytes, such as $ZrO_2$, $ThO_2$ and the like, stabilized with CaO, MgO and the like can be used as a raw material for the solid electrolyte sintered body 2. The shape of the solid electrolyte sintered body 2 may be a pellet-like shape, such as polygonal plate-like shape, globular shape, cylindrical shape, prism-like shape or the like. Further, the solid electrolyte sintered body is preferred to have an apparent porosity within the range of 5–40%. As the metal wires 3 and 4, there can be used not only platinum wires, but also wires of other catalytic metals, such as Ru, Pd, Rh, Ir and the like, and further wires of heat-resistant metals, such as Au, Ag and the like, which have no catalytic action. The metal wires 3 and 4 may be formed into such a structure that their middle portion is embedded in the solid electrolyte sintered body 2.

Figure 3:
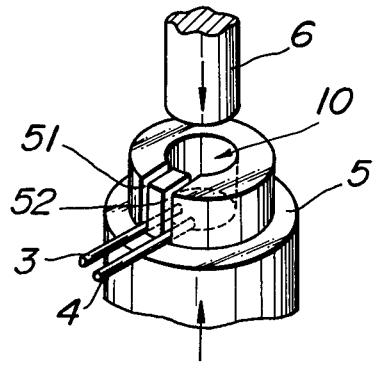
FIG. 3 is a diagrammatic view for explaining the production steps of the sensor.

This sensor 1 for measuring air-fuel ratio was produced in the following manner. That is, as illustrated in FIG. 3, granules 10 having a grain size of 40-150 mesh, which had been produced from a mixture of $ZrO_2$ powder and $Y_2O_3$ powder through calcination, pulverization and granulation, were filled in a lower die 5 having slits 51 and 52, and metal wires 3 and 4 were inserted into the lower die through the slits 51 and 52. The granules 10 were pressed by an upper die 6 to form a shaped article, and the shaped article was fired in air kept at 1,400°-1,600° C. for 30-60 minutes to produce the sensor 1.

Figure 4:
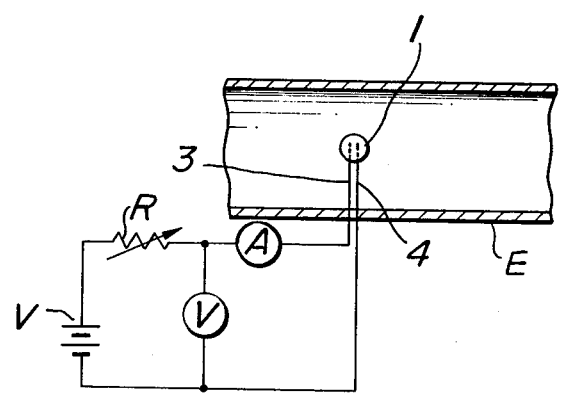
FIG. 4 is a diagram for explaining the method of measuring the characteristic property of the sensor.
Figure 5:
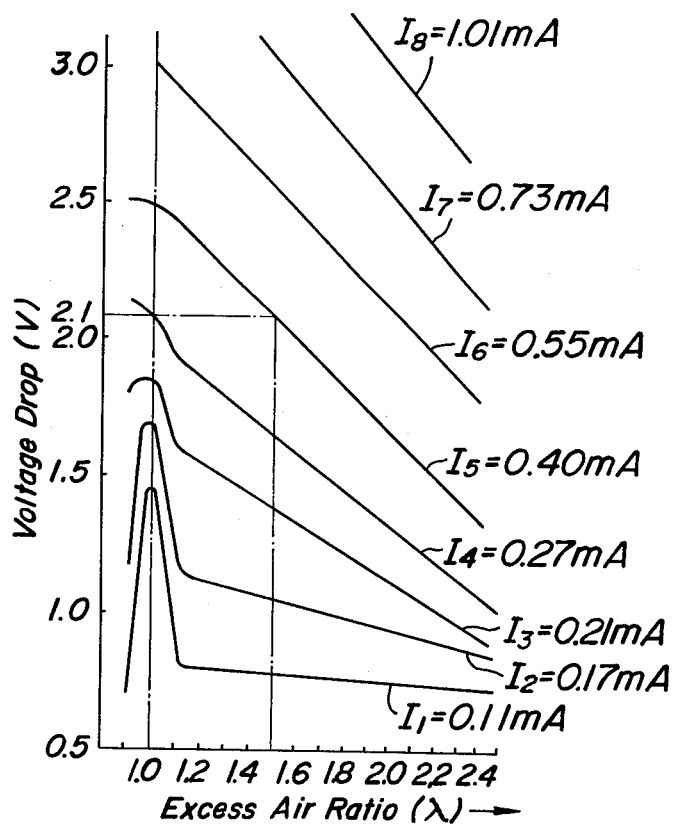
FIG. 5 is a graph illustrating the characteristic curve of the sensor.

The sensor 1 is arranged in a gas to be measured, which flows in an exhaust pipe E kept at 700° C., as illustrated in FIG. 4, and a direct current of 12 volts is applied between the metal wires 3 and 4 through a variable resistor R. FIG. 5 is a graph illustrating a relation between the excess air ratio $\lambda$ (air-fuel ratio) of the gas to be measured flowing in the exhaust pipe E and the voltage drop V under various electric currents I as a parameter flowing in the sensor 1. It can be seen from FIG. 5 that the sensor 1 causes a linear voltage drop depending upon the variation of excess air ratio $\lambda$ within the range of $\lambda \geq 1.1$, and that the sensor 1 causes a large voltage drop V within the range of 0.2-1.0 milliamperes or more of electric current I. Therefore, the sensor 1 has an excellent property for measuring air-fuel ratio within the range of the excess air ratio $\lambda$ of not less than 1.1.

In the above-described experiment, an exhaust gas, which had been formed by combusting completely a fuel and kept under a chemical equilibrium condition, was flowed in the exhaust pipe E. However, when such equilibrium condition is not ensured, it is preferable to give an oxidative catalytic property to the porous sintered body of the sensor 1 without deteriorating its electroconductive property due to oxygen ion, by impregnating the porous sintered body with an aqueous solution containing a salt of catalytic metals, such as platinum and the like, in a proper concentration, and then heating the impregnated porous sintered body to bake the catalytic metals, such as platinum and the like, on the surface of the porous sintered body.

Then, how to measure air-fuel ratio by using the above-described sensor 1 for measuring air-fuel ratio will be explained referring to FIGS. 6 and 7.

Figure 6:
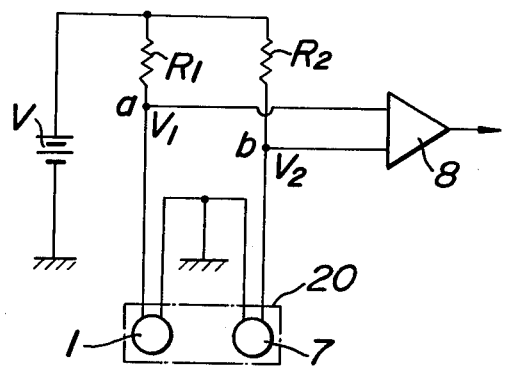
FIG. 6 is a diagram illustrating a device for measuring the air-fuel ratio of a gas by using a sensor for measuring air-fuel ratio according to the present invention.
Figure 7:
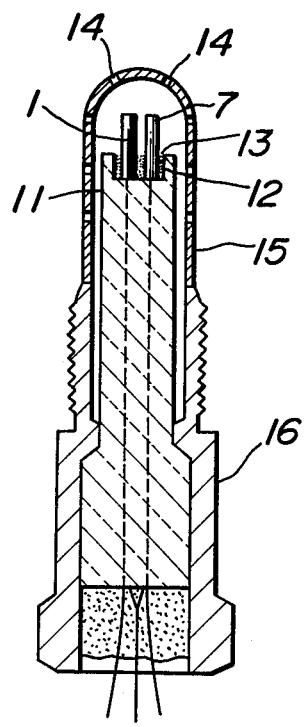
FIG. 7 is a cross-sectional view of a plug for measuring air-fuel ratio, which is provided at its interior with a sensor for measuring air-fuel ratio according to the present invention.

FIG. 6 illustrates one embodiment of a device for measuring the air-fuel ratio of a gas by using a sensor for measuring air-fuel ratio according to the present invention. In FIG. 6, the references $R_1$ and $R_2$ represent resistors having given resistance values, the numeral 7 represents a temperature-compensating element (a thermistor), which does not substantially vary in its resistance value against the variation of air-fuel ratio of gas to be measured, but exhibits about the same variation of resistance value (or voltage drop) as the sensor 1 depending upon the variation of temperature. As the temperature-compensating element, there can be used temperature-compensating elements having given resistance value and B-constant, which consist of densely sintered oxides of transition metals, such as Ti, Fe, Cr, Co, Mn and the like, alone or occasionally diluted with an insulating material, such as $Al_2O_3$, MgO, $SiO_2$ or the like. The above described resistors $R_1$ and $R_2$, sensor 1 and element 7 are connected so as to form a bridge circuit with respect to a direct current source V of 12 volts. The numeral 8 represents a measuring circuit, which is applied with a voltage $V_1$ at an intermediate point a between the resistor $R_1$ and the sensor 1 and with a voltage $V_2$ at an intermediate point b between the resistor $R_2$ and the element 7, and is used for measuring, from the difference between $V_1$ and $V_2$, the voltage drop, which varies depending upon the variation of excess air ratio $\lambda$. The sensor 1 and the temperature-compensating element 7 are arranged in parallel to each other and fixed to the recess 12 at the tip of a tubular insulating body 11 through an adhesive 13; and the insulating body 11 is arranged in and fixed airtightly to a cylindrical holding metal fitting 16 provided at its tip side with a protecting cap 15 having vent holes 14 by means of a conventional technique to form a plug 20 for measuring air-fuel ratio. This plug 20 for measuring air-fuel ratio is arranged in an exhaust pipe, and the sensor 1 and the temperature-compensating element 7 are contacted with a gas to cause the same variation of temperature with each other, and the voltage drop between the metal wires 3 and 4 of sensor 1 due to the variation of temperature can be compensated by the element 7. Further, when the sensor 1 is set so that the voltage drop is small appropriately in comparison with the direct current voltage V applied to the sensor 1, the voltage drop between the metal wires 3 and 4 of the sensor 1 caused depending upon the air-fuel ratio, that is, the excess air ratio $\lambda$, of a gas has a current property similar to that under a constant electric current, and moreover when an appropriately large amount of electric current is flowed, a voltage drop, which varies substantially linearly depending upon the variation of excess air ratio $\lambda$ within the range of the excess air ratio $\lambda$ of not less than 1, can be obtained.

As described above, in the present invention, since two metal wires are embedded in a porous solid electrolyte sintered body at a given interval to form a sensor for measuring air-fuel ratio, the sensor can be set so that the air-fuel ratio of a gas to be measured and the electrical property between the electrodes can be linearly varied in a wide range within the excess air ratio $\lambda$ of not less than 1. As a result, the air-fuel ratio of a gas to be measured can be accurately and simply measured in the lean side, wherein the air-fuel ratio is not less than the theoretical air-fuel ratio. Moreover, the sensor has the following merits that the sensor itself can be made into a small size, and therefore the sensor is rapid in the output and in the rising of response, and further not only the production of the sensor itself, but also the production of a plug for measuring air-fuel ratio from the sensor are easy and inexpensive.

What is claimed:

1. A sensor for measuring air-fuel ratio of a gas wherein the oxygen content in the gas is sensed through the measurement of the electrical resistance of the sensor, comprising a porous oxygen-ion-conductive solid electrolyte sintered body having a pellet-like shape formed from an oxygen ion-conductive solid electrolyte selected from the group consisting of $ZrO_2$ and $ThO_2$ and including a stabilizing material selected from the group consisting of $Y_2O_3$, CaO, and MgO, said body having an apparent porosity of from about 5% to about 40%, and two heat-resistant metal wires embedded therein at a given interval for measuring the electrical resistance thereof.

2. A sensor according to claim 1 wherein said sintered body has an apparent porosity of about 22%.

\* \* \* \* \*